US00PP37688P2

(12) United States Plant Patent
Tashiro

(10) Patent No.: US PP37,688 P2
(45) Date of Patent: Sep. 8, 2026

(54) ***PETUNIA* PLANT NAMED 'Balslincheel'**

(50) Latin Name: ***Petunia* x *hybrida***
Varietal Denomination: Balslincheel

(71) Applicant: Ball Horticultural Company, West Chicago, IL (US)

(72) Inventor: Rebecca Tashiro, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/350,045

(22) Filed: Oct. 5, 2025

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.1, 356.13, 356.21
See application file for complete search history.

*Primary Examiner* — Susan Mccormick Ewoldt
(74) *Attorney, Agent, or Firm* — Megan Bowman

(57) ABSTRACT

A new and distinct cultivar of *Petunia* plant named 'Balslincheel', characterized by its red and yellow bicolored flowers, medium, green-colored foliage, trailing, mounded growth habit, is disclosed.

1 Drawing Sheet

Latin name of genus and species of plant claimed: *Petunia* x *hybrida*.

Variety denomination: 'Balslincheel'.

BACKGROUND OF THE INVENTION

The present invention relates to a new and distinct cultivar of *Petunia* plant botanically known as *Petunia* x *hybrida* and hereinafter referred to by the cultivar name 'Balslincheel'.

The new cultivar originated in a controlled breeding program in Arroyo Grande, California during July 2020. The objective of the breeding program was the development of *Petunia* cultivars with novel coloration and have a compact-mounded growth habit.

The new *Petunia* cultivar is the result of cross-pollination. The female (seed) parent of the new cultivar is SlingShot Heartwheel 'Balslinteel', not patented, characterized by its medium pink and white flowers, medium, green-colored foliage, moderately vigorous and compact-mounded growth habit. The male (pollen) parent of the new cultivar is the proprietary *Petunia* x *hybrida* breeding selection coded PET-01317-01, not patented, characterized by its medium pink-purple flowers, medium, green-colored foliage, moderately vigorous and compact-mounded growth habit. The new cultivar was selected as a single flowering plant within the progeny of the above stated cross-pollination during March 2021 in a controlled environment in Guadalupe, California.

Asexual reproduction of the new cultivar by terminal stem cuttings since March 2021 in Guadalupe, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balslincheel' as a new and distinct cultivar of *Petunia* plant:

1. Bright red and yellow bicolored flowers;
2. Medium green-colored foliage;
3. Medium vigorous with a mounded, trailing growth habit.

Plants of the new cultivar differ from plants of the female and male parents primarily in having red and yellow bicolored flowers.

Of the many commercially available *Petunia* cultivars, the most similar in comparison to the new cultivar is SlingShot Lemonberry 'Balslinlemb', not patented. However, in comparison, plants of the new cultivar differ from plants of 'Balslinlemb' in at least the following characteristics:

1. Plants of the new cultivar have lighter, red-colored flowers than plants of 'Balslinlemb';
1. Plants of the new cultivar have flowers with more yellow coloration on the mid-vein than plants of 'Balslinlemb',
3. Plants of the new cultivar has lighter, green foliage than plants of 'Balslinlemb'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balslincheel'. The approximately 5-month-old plants were grown in 6-inch pots for approximately 17 weeks in a greenhouse in West Chicago, Illinois.

DETAILED BOTANICAL DESCRIPTION

Figure 1:
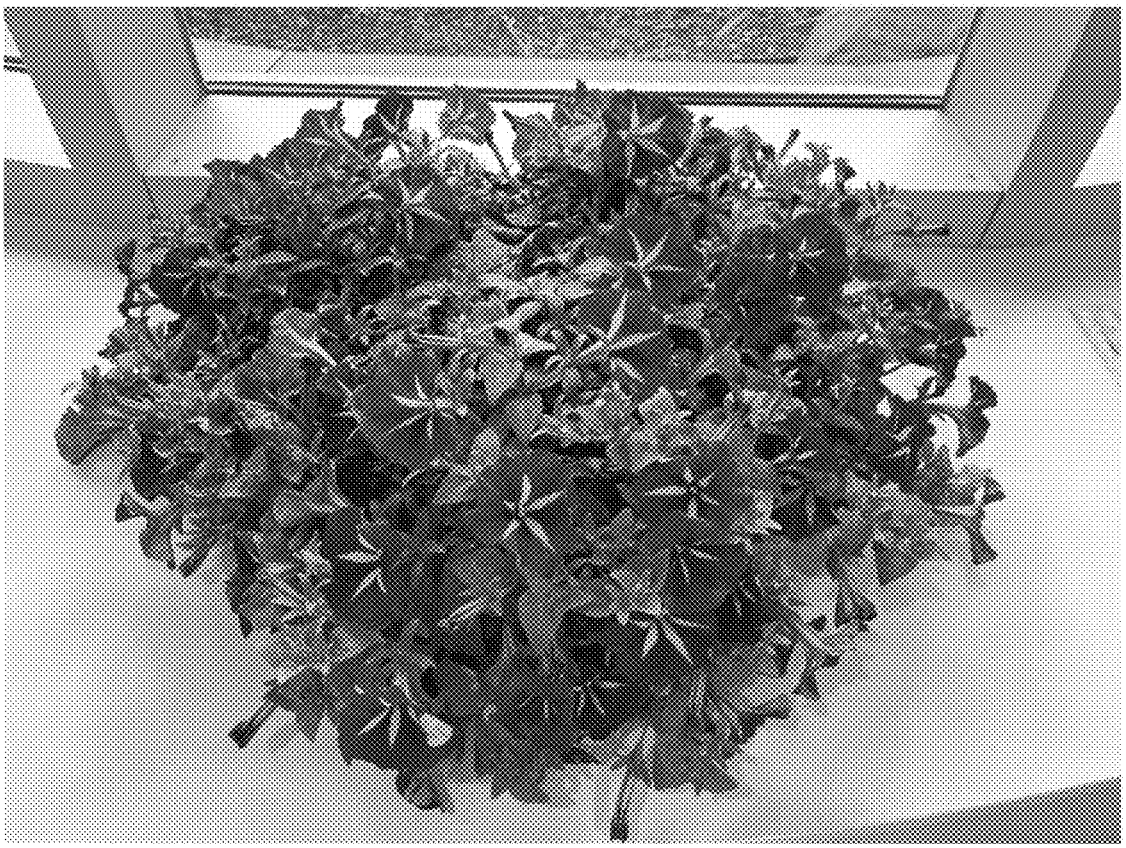
FIG. 1 illustrates a side view of the overall growth and flowering habit of 'Balslincheel'.
Figure 2:
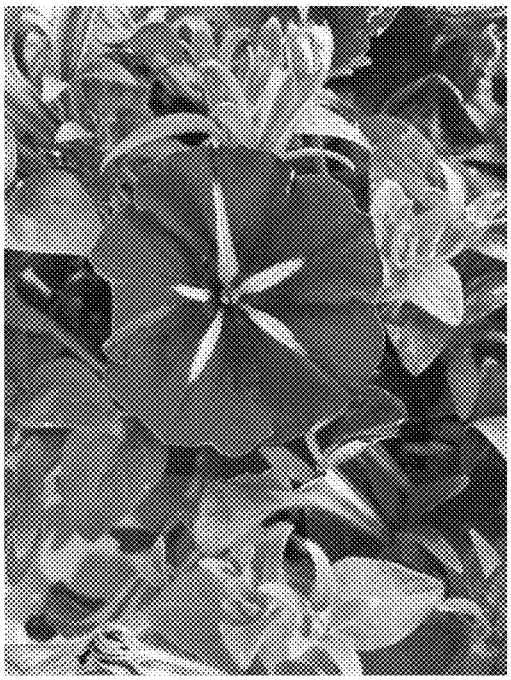
FIG. 2 illustrates a close-up view of an individual flower of 'Balslincheel'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2025 under natural light conditions in West Chicago, Illinois.

The following descriptions and measurements describe approximately 5-month-old plants produced from cuttings from stock plants and grown in a double polyethylene under conditions comparable to those used in commercial practice. The plants were grown in West Chicago, Illinois in 6-inch pots for approximately 4 weeks utilizing a soilless growth medium: Plants were pinched two weeks before transplant. Greenhouse temperatures were maintained at approximately 65° F. to 70° F. (18.3° C. to 21.1° C.) during the day and approximately 60° F. to 65° F. (15.6° C. to 18.3° C.) during the night. Supplemental lighting was used. Measurements and numerical values represent averages of typical plants.

Botanical classification: *Petunia* x *hybrida* 'Balslincheel'.

Parentage:

*Female parent*.—SlingShot Heartwheel 'Balslinteel', not patented.

*Male parent*.—Proprietary *Petunia* x *hybrida* breeding selection coded PET-01317-01, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Trailing, mounded growth habit.

*Size*.—Height from soil level to top of plant plane: Approximately 18.0 cm. Width: Approximately 64.0 cm.

*Branching habit*.—Freely branching. Quantity of main branches per plant: Approximately 8.

*Branch*.—Strength: Moderate. Length: Approximately 24 cm. Diameter: Approximately 3.0 mm. Length of central internode: Approximately 2.0 cm. Texture: Densely glandular pubescent. Gland color: Colorless, transparent. Color of young stems: 144A. Color of mature stems: 143A.

Foliage description:

*General description*.—Quantity of leaves per main branch: Approximately 14. Fragrance: Slight. Form: Simple. Arrangement on flowering stem: Alternate.

*Leaves*.—Aspect: Acute angle to stem. Shape: Ovate. Margin: Entire. Apex: Acute. Base: Broadly attenuate. Venation pattern: Pinnate. Length of mature leaf: Approximately 4.5 cm. Width of mature leaf: Approximately 2.7 cm. Texture of upper and lower surfaces: Lightly glandular pubescent. Gland color: Colorless, transparent. Color of upper surface of young and mature foliage: 143A with venation of 145B to indistinguishable. Color of lower surface of young and mature foliage: Closest to 143B with venation of 145B to indistinguishable.

*Petiole*.—Length: Approximately 5.0 mm. Width: Approximately 3.0 mm. Texture: Densely glandular pubescent hairs. Gland color: Colorless, transparent. Color: 143C.

Flowering description:

*Flowering habit*.—'Balslincheel' is freely flowering under outdoor growing conditions with substantially continuous blooming from spring through summer and year-round in greenhouse environment.

*Lastingness of individual flower on the plant*.—Approximately 10 to 12 days.

Flower description:

*General description*.—Type: Simple, salverform. Quantity per plant: Approximately 60. Fragrance: Minimal, sweet.

*Bud*.—Rate of opening: Generally, takes 2 to 3 days for bud to progress from first color to fully open flower. Quantity per plant: Approximately 30.

*Bud just before opening*.—Shape: Oblong. Length: Approximately 4.7 cm. Diameter at apex: Approximately 8.0 mm. Diameter at base: Approximately 3.0 mm. Texture: Densely glandular pubescent. Gland color: Colorless, transparent. Color of petal portion: 183B with venation of 187B. Color of tube: Closest to 144B and 183B.

*Corolla*.—Diameter: Approximately 6.4 cm.

*Petals*.—Quantity: 5, fused to form a tube. Shape: Obovate. Appearance: Matte. Margin: Entire, slightly wavy. Apex: Cuspidate to rounded. Length from tube: Approximately 2.3 cm. Length of free portion: Approximately 0.5 cm. Width: Approximately 2.5 cm. Texture of upper surface: Glabrous. Texture of lower surface: Slightly glandular pubescent. Gland color: Colorless, transparent. Color of upper surface when first and fully open: between 60B and 71A with midveins of 143C that extend to the petal margin as the flower matures, surrounded by 2B. Color of lower surface when first and fully open: 60C with venation of 143C surrounded by 1C.

*Corolla tube*.—Length: Approximately 3.5 cm. Diameter at distal end: Approximately 1.5 cm. Diameter at proximal end: Approximately 2.0 mm. Texture of inner surface: Glabrous. Texture of outer surface: Densely glandular pubescent. Gland color: Colorless, transparent. Color of inner surface: Closest to 61A, with venation of 143C surrounded by 2A. Color of outer surface: Closest to 59C with venation of 143C surrounded by 1B.

*Sepals*.—Quantity per flower: 5, fused at base. Shape: Linear. Margin: Entire. Apex: Acute. Length: Approximately 2.5 cm. Width: Approximately 7.0 mm. Texture of upper and lower surfaces: Densely glandular pubescent. Gland color: Colorless, transparent. Color of upper surface: 137B. Color of lower surface: 138A with 144B at base.

*Peduncle*.—Strength: Strong, flexible. Aspect: Acute angle to stem. Length: Approximately 2.5 cm. Diameter: Approximately 2.0 mm. Texture: Densely glandular pubescent with a mixture of long and short hairs. Gland color: Colorless, transparent. Color: 144A.

*Reproductive organs*.—Androecium: Stamen quantity: 5, basifixed. Stamen length: Approximately 2.7 cm. Filament length of fixed portion: Approximately 1.3 cm. Filament color: NN155C. Anther shape:

Bilobed. Anther length: Approximately 1.0 mm. Anther color: 151D. Pollen amount: Abundant. Pollen color: 156D. Gynoecium: Pistil quantity: 1 per flower. Pistil length: Approximately 2.4 cm. Stigma shape: Funnel. Stigma length: Approximately 2.0 mm. Stigma color: 138A. Style length: Approximately 2.2 cm. Style color: 145V. Ovary length: Approximately 4.0 mm. Ovary color: 143B with an overlay of 166A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balslincheel', substantially as herein illustrated and described.

* * * * *